United States Patent [19]

West et al.

[11] Patent Number: 4,709,107

[45] Date of Patent: Nov. 24, 1987

[54] PROCESS FOR PRODUCING NITRONES

[75] Inventors: Paul R. West, Ballston Spa; Gary C. Davis, Albany, both of N.Y.

[73] Assignee: General Electric Company, Schenectady, N.Y.

[21] Appl. No.: 786,937

[22] Filed: Oct. 11, 1985

[51] Int. Cl.$^4$ .................... C07C 76/02; C07C 79/06; C07C 79/10

[52] U.S. Cl. .................................. 568/927; 568/928; 568/943; 568/947; 568/335; 568/924; 564/300; 564/301; 560/20

[58] Field of Search .................... 546/98, 99; 568/928, 568/924, 927, 943, 947, 948, 335; 564/300, 301

[56] References Cited

PUBLICATIONS

"Synthesis of N(2)-Hydroxy-1,2,3,4-Tetrahydro-B-Carbolines", Heterocycles, vol. 23, #7, pp. 1671-1673, 1985, So-Yeop Han, M. V. Lakshmikantham, and Michal P. Cava.
"Hydroxylaminomethylation Reactions of 4-chloro-1-naphthal", Archiv der Pharmazie, Muehrle, Hans et al, 1981, 314(10) 836-41.
"An Efficient Method for Generation of N-Methylnitrones", vol. 50, #26, pp. 5913-5916, The Journal of Organic Chemistry, Druekhammer, Dale & Wong, Chi-Huey.

Primary Examiner—John F. Terapane
Assistant Examiner—Susan Wolffe
Attorney, Agent, or Firm—William T. Teoli; James C. Davis, Jr.; James Magee, Jr.

[57] ABSTRACT

A method for preparing nitrones from mixtures of arylhydroxylamines and alkylhydroxylamines containing zinc oxide solids is provided which does not require filtration of the mixture prior to reaction. This is accomplished by introducing a dilute acid solution to the mixture so as to solubilize the zinc oxide powder. The hydroxylamines within solution may be reacted with an aldehyde to produce a nitrone where the dilute acid dissolves the zinc oxide.

10 Claims, No Drawings

PROCESS FOR PRODUCING NITRONES

BACKGROUND OF THE INVENTION

This invention is related to a method for preparing nitrones, including diarylnitrones, dialkylnitrones and alkylarylnitrones. More particularly, this invention is directed to a method for preparing nitrones from a reaction mixture of arylhydroxylamines and/or alkylhydroxylamines obtained by the reduction of nitro compounds with zinc powder.

Arylhydroxylamines and alkylhydroxylamines are prepared by the reduction of the corresponding nitro compounds, i.e., nitroaromatic compounds and nitroalkanes. The reduction of such nitro compounds can be accomplished by a number of methods including electrochemical reduction, catalytic hydrogenation and metal reduction. Although catalytic hydrogenation often provides a high degree of selectivity and rate of reaction, as disclosed in copending application Ser. No. 777,390, reduction with metals may be desirable due to the simplicity of the process and the simple equipment which can be utilized to perform the reduction. Metal reductions are simple in that they need not take place under pressure or require a hydrogen source. Reduction of nitro compounds with metal powder, such as zinc powder, does pose problems in that the metal oxide coproduct often precipitates within the reaction mixture, necessitating a lengthy filtration step to remove the metal oxide.

It is desirable to avoid this lengthy filtration step since arylhydroxylamines are known to undergo side reactions over time due to their high reactivity. For example, in producing diarylnitrones from the reaction of arylhydroxylamine and arylaldehyde, it is advantageous to commence the reaction immediately upon formation of the arylhydroxylamine. However, this cannot be accomplished where the residual metal oxide remains as a voluminous precipitate in the reaction mixture.

SUMMARY OF THE INVENTION

A method for producing nitrones is provided which comprises reducing a nitro compound with zinc to produce a hydroxylamine and zinc oxide, dissolving substantially all of the zinc oxide with a dilute acid solution and reacting an aldehyde with the hydroxylamine to produce nitrone.

OBJECTS OF THE INVENTION

An object of the present invention is to provide an improved method for producing nitrones from arylhydroxylamines and alkylhydroxylamines obtained by zinc reduction of the corresponding nitro compound.

Another object of the present invention is to provide a method for reacting arylhydroxylamines and alkylhydroxylamines in admixture with zinc oxide without separating the zinc oxide by filtration.

A further object of the present invention is to provide a method for producing nitrones by zinc reduction without isolating the zinc oxide precipitate generated.

Further objects will be obvious from the detailed description herein.

DETAILED DESCRIPTION OF THE PREFERRED EMBODIMENTS

The present invention is based on the discovery that a zinc oxide precipitate within a reaction mixture of arylhydroxylamine and/or alkylhydroxylamine can be adequately solubilized so as to permit further reaction without filtration. This discovery finds particular utility in methods for producing alkylnitrones and arylnitrones, including alkylarylnitrones.

Zinc powder is commonly employed in reduction reactions of nitroalkanes and nitroaromatic compounds. When these nitro compounds are reduced to the corresponding hydroxylamine, zinc is converted to the oxide form (ZnO). The zinc oxide precipitates when formed within the reaction mixture in the absence of the dilute acid solution. The stoichiometric amount of zinc necessary to produce the corresponding hydroxylamine generally provides a molar ratio of zinc to nitro compound of about 2:1. Excess quantities of 10 to 30 mole percent of zinc may be desired to ensure complete reduction of the nitro compound. Excessively large quantities of zinc, such as a 10:1 mole ratio of zinc to nitro compound, are not desirable in that the nitro substituents may overreduce to the corresponding amine and the excess Zn may have to be filtered.

Essentially, any reduction conditions known to reduce nitro compounds to hydroxylamines with zinc are suitable. Reduction of the nitro compounds with zinc can be accomplished over a wide temperature range, generally from about 0° C. to 150° C. The reaction can also take place under pressure, however, operating at both ambient temperature and ambient pressure is most preferred for its convenience. Reduction of the nitro compound provides a reaction mixture of hydroxylamines which contains a zinc oxide precipitate.

The term "nitro compounds" as used herein refers to species which are reduced with zinc in accordance with this invention and is intended to include nitroaromatic compounds having an aromatic nucleus of from about 6 to 30 carbon atoms. Those which are preferred are of the formula $(NO_2)_c R^6 X_b$ wherein $R^6$ is a aromatic hydrocarbon radical of from 6 to 20 carbon atoms, X is selected from the group consisting of halogen, cyano groups, aliphatic acyl radicals of from 1 to 8 carbon atoms, alkyl radicals and substituted alkyl radicals of from 1 to 8 carbon atoms, aryl and substituted aryl radicals of from 6 to 13 carbon atoms and alkoxy carbonyl radicals of from 2 to 8 carbon atoms, b is a value of from 0 to 3 and c is 1 or 2. Those which are most preferred include nitrobenzene, p-ethoxynitrobenzene, p-nitroethylbenzoate, p-nitromethylbenzoate, p-nitrobutylbenzoate and p-nitroacetophenone.

Also included in the term "nitro compounds" are the nitroalkanes of the formula $R^7(NO_2)_d$, wherein $R^7$ is an alkyl or substituted alkyl radical of from 1 to 15 carbon atoms and d is 1 or 2. Examples of nitroalkanes which provide alkylhydroxylamines useful in this invention include nitromethane, nitroethane, 1-nitropropane, 2-nitropropane, 1-nitrobutane, 1-nitropentane, nitrocyclohexane, 1-nitrohexane, 3-nitro-2-methylpentane, 2-nitro-2-methylpropane and the like.

The nitroaromatic and nitroalkanes are reduced to the corresponding hydroxylamines which includes both arylhydroxylamines and alkylhydroxylamines. The reduction reaction can take place in the presence of a water miscible organic solvent. Suitable organic solvents include lower aliphatic alcohols such as methanol, ethanol, isopropanol, propanol, and the like. Other water miscible organic solvents are suitable, such as acetonitrile, however, ethanol is most preferred. The quantity of organic solvent utilized can vary widely, with preferred quantities of organic solvent providing concentrations in water of about 0 to 50 wt. %. Nitro compound concentrations are preferably 5 to 25 weight percent of the reaction medium.

The reduction of the nitro compounds can be accomplished in conventional equipment either batchwise or continuously. The nitro compound can be introduced into the reaction vessel together with solvent followed by the addition of zinc powder. The time to complete reduction of the nitro compound depends on the temperature of the reaction medium and size of the reaction. Larger reaction volumes take longer to complete.

Acids may be used to enhance the rate of reduction. According to Herbert House, in *Modern Synthetic Reactions,* 2nd Ed. (1972), p. 211, Benjamin Publishing, the acids protonate intermediate anions or radical anions formed in the reduction of the nitro compounds. The preferred acids are those generated by the dissociation of ammonium salts such as ammonium chloride and carboxylic acids such as hexanoic acid, formic acid, pentanoic acid, acetic acid, phenylacetic acid, propanoic acid, butanoic acid, etc. It is generally desirable to have enough acid present in the aqueous medium to maintain the pH in the range of about 2-7 throughout the reduction. Lower pH values may cause the arylhydroxylamines to decompose or overreduce to the corresponding amine. The most preferred acids have a dissociation constant less than or equal to acetic acid so as to avoid degradation of the arylhydroxylamines.

In the preferred embodiment, a dilute aqueous acid solution is added to the mixture to solubilize the zinc oxide upon completion of the reduction reaction. The dilute aqueous acid solution may be present during the reduction of nitro compounds in some embodiments of this invention such as where the acid used is acetic acid or one of equivalent strength.

The term "dilute aqueous acid solution" generally refers to aqueous solutions of 10% to 50% by weight of acid having a dissociation constant value greater than or approximately equal to acetic acid. The stronger acids are preferred to ensure the ZnO is solubilized. Dilution of the acid is desired to avoid degradation of the arylhydroxylamines.

Suitable acids include both mineral and organic acids. Particularly suitable are the strong mineral acids, such as hydrogen halides and the oxo-acids of sulfur and phosphorus. Of the hydrogen halides, HCl, HBr and HF are preferred. The preferred phosphoric oxide acids include phosphorus acid and phosphoric acid. Examples of sulphur oxide acids which can be used include sulfurous ($H_2SO_3$), sulfuric ($H_2SO_4$) and the like.

Organic acids, such as sulfonic acids and carboxylic acids can also be used. The carboxylic acids have a dissociation constant value which approximates that of acetic acid or above. Particular examples of suitable carboxylic acids include acetic acid, propanoic acid, butanoic acid, 2-methylpropanoic acid, pentanoic acid, hexanoic acid, heptanoic acid, chloroacetic acid, trichloroacetic acid, trifluoroacetic acid, phenylacetic acid, 2-chlorobutanoic acid, 3-chlorobutanoic acid, dichloroacetic acid, 4-chlorobutanoic acid, 5-chlorobutanoic acid and the like. Suitable sulfonic acids include methanesulfonic acid, ethylsulfonic acid, benzenesulfonic acid, butylsulfonic acid and the like.

The quantity of dilute aqueous acid solution necessary to perform this process is dependent on the quantity of zinc oxide present in solution. The quantity utilized must be sufficiently large to solubilize the zinc oxide to the extent that filtration is unnecessary. Quantities of dilute acid solution which provide an equivalent mole ratio, i.e. a zinc oxide to hydronium ion mole ratio, within the range of about 1:1-4 are preferred. Excess quantities of the aqueous acid solution are generally not harmful to this process when dilute and they may actually facilitate the reaction of arylhydroxylamine and/or alkylhydroxylamine to produce nitrone as disclosed in copending application Ser. No. 777,390.

Preferably, the arylhydroxylamine and/or alkylhydroxylamines within the reaction medium are reacted with an aldehyde to produce nitrone once the reaction medium is clear. However, the aldehyde may be present during the reduction reaction where the dilute aqueous acid solution is also present. Both alkylnitrones and arylnitrones can be produced, including alkylarylnitrones. This reaction can be performed by methods known to the art, such as those described in copending application Ser. No. 777,390.

Both alkylaldehydes and arylaldehydes may be used to react with the hydroxylamine. The arylaldehydes which can be utilized in this reaction have an aromatic nucleus of from 6 to 30 carbon atoms and the alkylaldehydes have an alkyl backbone of from 2 to 15 carbon atoms. The preferred arylaldehydes are those of the formula

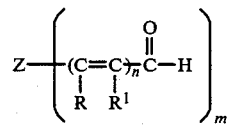

I and the preferred alkylaldehydes are of the formula

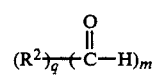

II wherein:

Z is $(R^3)_{\overline{a}}Q{-}R^4{-}$ or $R^5$;

Q is a monovalent, divalent or trivalent substituent or linking group;

each of R, $R^1$ and $R^3$ is independently hydrogen, an alkyl or substituted alkyl radical containing 1 to 8 carbon atoms or an aromatic radical containing 6 to 13 carbon atoms;

$R^2$ is an aliphatic or cyclic hydrocarbon radical of from 1 to 15 carbon atoms;

$R^4$ is an aromatic radical containing 6 to 13 carbon atoms;

$R^5$ is an aromatic heterocyclic radical containing 4 to 20 carbon atoms in which the hetero atoms are at least one selected from the group of oxygen, nitrogen and sulfur;

a is from 0 to 2, m is 1 or 2, q is 0 or 1 and n is from 0 to 4. Where m is 1, q is 1 and where m is 2, q is 0 or 1.

As is apparent from formula I, the arylaldehydes may have conjugated carbon linkages wherein the conjugation is between the aryl group and the carboxy group. Included within the aldehydes of formulas I and II are the bisaldehydes (when m=2), where both aldehyde functional groups are bound to the aromatic nucleus Z, the alkyl backbone $R^2$ or to each other. Both R and $R^1$ are typically hydrogen or a methyl radicals.

The identity of the Q value is not critical and suitable values will be apparent to those skilled in the art. Q will be monovalent, divalent or trivalent as the value of a is 0, 1 or 2. Examples of monovalent values for Q are fluorine, chlorine, bromine, iodine, alkyl radicals of from 1 to 6 carbon atoms and aryl radicals of from 6 to 13 carbon atoms. Examples of divalent values for Q are oxygen, sulfur, carbonyl, alkylene and arylene. An example of a trivalent value for Q is nitrogen. Preferably, Q is fluorine, chlorine, bromine, iodine, oxygen, sulfur or nitrogen.

The alkylhydroxylamines and/or arylhydroxylamines can be reacted with the aldehydes described above within the reduction reaction medium that contains the solubilized zinc oxide. Suitable solvents include water and those water miscible organic solvents described above, i.e. the lower aliphatic alcohols and other highly polar water miscible solvents such as acetonitrile, dioxane and carboxylic acids. The preferred solvents are ethanol, methanol, acetic acid, dioxane, and acetonitrile, with alcohol solvents being most preferred.

An acid catalyst may be used for this condensation reaction if desired. In that the dilute acid is already present in the reduction reaction mixture, this acid also serves to catalyze the condensation reaction. Suitable acids include the mineral acids, the strong carboxylic acids and the sulfonic acids described more particularly above and in copending application Ser. No. 777,390.

Additional acid may be added to the reaction mixture where a stronger acid is desired or where the quantity is insufficient to provide catalysis of the reaction. This situation will be rare in that quantities of acid within the range of about 0.01 to 10 wt. % of the organic solvent and water within the reaction mixture provide catalysis.

The condensation reaction between aldehydes and the hydroxylamines described above can proceed at temperatures ranging from about 0° C. to about 150° C. at pressures either above or below atmospheric pressure. The nitrone produced can be recovered by conventional methods such as precipitation and filtration. Precipitation of the nitrone can be initiated by cooling and/or adding water to the reaction medium. These methods are discussed with greater particularity in copending application Ser. No. 777,390. Alternatively the nitrone can be recovered by extraction with a suitable organic solvent such as ether, methylene chloride, toluene and the like.

In the preferred reaction scheme, the aldehyde is added to the organic solution of hydroxylamine with the dilute acid solution present. Additional acid catalyst may be subsequently added and a quantity of water may be added so as to shift the equilibrium by precipitation of the nitrone.

This reaction scheme can produce diarylnitrones of the formula

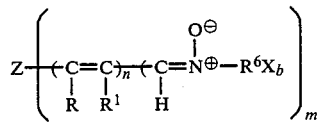

alkylarylnitrones of the formula

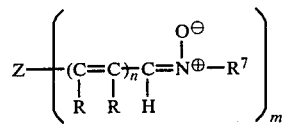

and/or dialkylnitrones of the formula

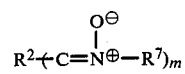

wherein Z, R, $R^1$, $R^2$, $R^6$, X, m, n and b are as previously defined and $R^7$ is an alkyl radical of from 1 to 15 carbon atoms.

The following examples are provided to illustrate preferred embodiments of this invention. It is not intended to limit the invention to the embodiments disclosed.

EXAMPLE 1

Nitrobenzene (12.5 grams, 0.1 mole) and 50 ml. of 95% ethanol was mixed with ammonium chloride (6.25 grams, 0.12 mole) in 50 ml. of water. The mixture was cooled in an ice bath and stirred vigorously while adding zinc dust (15.5 grams, 0.24 mole) in 3 gram portions every 3 to 4 minutes. After stirring for 25 minutes at 10° to 15° C., the resulting white suspension was treated with p-diethylaminobenzaldehyde (12.5 grams, 0.07 mole) in 50 ml. of acetic acid. A clear, yellow solution was immediately obtained. After 15 minutes, the nitrone began to precipitate. The reaction mixture was stirred for 30 minutes at room temperature, then poured into 200 ml. of toluene. The toluene was washed with two 150 ml portions. of water, 150 ml. of saturated aqueous sodium bicarbonate and again with 150 ml. of water. Most of the toluene was then evaporated at reduced pressure and the remaining warm solution poured into 200 ml. of cyclohexane while stirring and cooling. The crude nitrone (15.1 grams, 0.056 mole, 80%) was collected by filtration and exhibited a melting point within the range of 95° to 102° C.

EXAMPLE 2

To a 250 ml. 3-neck flask, fitted with a mechanical stirrer, $N_2$ inlet and a thermometer was added 5 g of t-nitrobutane and 1.7 g of $NH_4Cl$ predissolved in 35 ml. of water. The mixture was stirred vigorously and cooled to 0° C. on an ice bath. Zinc dust (8 g) was slowly added so that the temperature remained below 10° C. This mixture was stirred at 0° C. for 3 hours, after which the ice bath was removed and the mixture allowed to exotherm (~40° C.) for ½ hour. Acetic acid (45 ml.) was added with stirring until most of the zinc oxide had dissolved. Cinnamaldehyde (0.85 equivalents) was then added. The reaction was stirred vigorously for 24 hours after which analysis by liquid chromatography showed 61% nitrone. A small amount of undissolved zinc was removed by filtration. The filtrate was extracted with $CH_2Cl_2$ two times, and the methylene chloride was combined. The organic layer was then washed once with water, washed twice with saturated sodium bicarbonate, dried with $MgSO_4$ and the $CH_2Cl_2$ was evaporated leaving a semi-solid. Purification of this solid with hexane afforded the nitrone as a yellowish white powder (3.25 g, 39% yield based upon aldehyde).

The examples above illustrate particular embodiments of this invention. Variations of these embodiments will be obvious to those skilled in the art and are considered within the scope of this invention.

We claim:

1. A zinc metal reduction method for making arylnitrones or alkylnitrones which does not require a zinc oxide filtration step prior to nitrone recovery, which comprises,
   (1) effecting the reduction of a nitroaromatic compound or nitroalkane with powdered zinc and sufficient ammonium chloride to produce the corresponding aromatic hydroxylamine or alkane hydroxylamine,
   (2) thereafter effecting reaction between the aromatic hydroxylamine or alkanehydroxylamine with aromatic aldehyde or aliphatic aldehyde in the presence of sufficient acetic acid to substantially dissolve the zinc oxide of (1), and
   (3) recovering nitrone from the mixture of (2) selected from diarylnitrone, alkylarylnitrone, and dialkylnitrone.

2. A method as in claim 1 wherein the aldehyde is present during the reduction of the nitro compound with zinc.

3. A method as in claim 1 wherein the nitro compound is a nitroaromatic species of the formula $(NO_2)_cR^6X_b$, wherein $R^6$ is an aromatic radical of from 6 to 20 carbon atoms, X is selected from the group consisting of alkyl radicals of from 1 to 8 carbon atoms, substituted alkyl radicals of from 1 to 8 carbon atoms, aryl radicals of from 6 to 13 carbon atoms, substituted aryl radicals of from 6 to 13 carbon atoms, aliphatic acyl radicals of from 1 to 8 carbon atoms, alkoxy-carbonyl radicals of from 2 to 8 carbon atoms, cyano-groups and halogen, b is from 0 to 3 and c is 1 or 2.

4. A method as in claim 3 wherein the nitroaromatic compound is selected from the group consisting of nitrobenzene, p-ethoxynitrobenzene, p-nitroethylbenzoate, p-nitrobutylbenzoate and p-nitroacetophenone.

5. A method as in claim 1 wherein the nitro compound is a nitroalkane having the formula $R^7(NO_2)_d$ wherein $R^7$ is an alkyl or substituted alkyl radical of from 1 to 15 carbon atoms and d is 1 or 2.

6. A method as in claim 5 wherein the nitroalkane is selected from the group consisting of nitromethane, nitroethane, 1-nitropropane, 1-nitrobutane, 1nitropentane, 1-nitrohexane, nitrocyclohexane, 1-nitroheptane and 2-methyl-2-nitropropane.

7. A method as in claim 1 wherein the aldehyde is an arylaldehyde of the formula

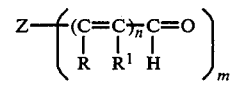

wherein R and $R^1$ are independently hydrogen, methyl or phenyl, m is 1 or 2, n is 0 or 1 and Z is $(R^3)_aQ\text{-}R^4$ or $R^5$, wherein $R^3$ is an alkyl radical of from 1 to 8 carbon atoms, $R^4$ is phenyl, Q a monovalent, divalent or trivalent substituent or linking group and a is a value of from 0 to 2.

8. A method as in claim 7 wherein the arylaldehyde is selected from the group consisting of
   4-diethylaminobenzaldehyde,
   4-dimethylaminobenzaldehyde,
   4-methoxybenzaldehyde,
   9-julolidinylcarboxaldehyde,
   3-phenylcinnamaldehyde and cinnamaldehyde.

9. A method as in claim 1 in which the aldehyde is an alkylaldehyde of the formula

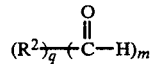

wherein $R^2$ is an aliphatic or cyclic hydrocarbon radical of from 1 to 15 carbon atoms, m is 1 or 2 and q is 0 or 1.

10. A method as in claim 9, wherein the alkylaldehyde is selected from the group consisting of ethanal, propanal, butanal, pentanal, hexanal, cyclopropylmethanal and glyoxal.

* * * * *